United States Patent [19]

Yoshida

[11] Patent Number: Plant 7,723

[45] Date of Patent: Nov. 26, 1991

[54] AFRICAN VIOLET NAMED KATY

[76] Inventor: Eiichi Yoshida, P.O. Box 4836, Hayward, Calif. 94540-4836

[21] Appl. No.: 524,127

[22] Filed: May 14, 1990

[51] Int. Cl.[5] ..... A01H 5/00

[52] U.S. Cl. ..... Plt./69

[58] Field of Search ..... Plt./69

*Primary Examiner*—James R. Feyrer

[57] ABSTRACT

A new variety of African violet plant for potted plant culture particularly distinguished by it year-round blooming capability, its profuse production of dark red flowers, its shorter growing period for commercial purposes, and its compact growth with abundant foliage of solid green color which provides a spreading base and attractive backing for the clusters of blossoms.

1 Drawing Sheet

BACKGROUND OF THE NEW PLANT

This new variety of African violet plant was obtained by cross-pollenating the seed parent Saintpaulia "Melodie" Rhonda and the pollen parent Saintpaulia "Melodie" Angie. The seed pods of the pollenated plants were used as the generic basis for initiating further propagation trials. A total of 920 seedlings resulted from the stated cross. Of these, 27 individual seedlings were selected and retained for further observation to assess vigor, early blooming, and development. The mature characteristics of growth habit and for testing to reflect disease resistance of the selections.

The specific plant was a selection from among the 27 plants remaining from the initial cross. The plant of this disclosure was selected based on a number of outstanding characteristics including exhibition quality plant confirmation and generous placement of elegant flowers of appealing shape and color characteristics and was subsequently denominated 'Katy'. I have asexually reproduced 'Katy' by taking leaf cuttings to start plants in the normal way for *Saintpaulia ionantha.* Descendants of the original plant have proven to be completely the same as the parent plant in all distinguishing characteristics to establish that 'Katy' is stable.

BRIEF DESCRIPTION OF THE DRAWING

Sheet one is a full color photographic view of the plant in bloom, the colors shown being as nearly true as it is reasonably possible to obtain conventional photographic procedures.

DESCRIPTION OF THE PLANT

The following is a detailed description of my new African violet plant with the color designation being accorded to the R.H.S. Colour Chart published by The Royal Horticultural Society of London, England, with collaboration by the British Colour Council.

THE PLANT

Name: Katy.
Origin: Seedling.
Parentage:
- *Seed parent.*—Saintpaulia "Melodie" Rhonda.
- *Pollen parent.*—Saintpaulia "Melodie" Angie.

Classification:
- *Botanic.*—*Saintpaulia ionantha.*
- *Commercial.*—African violet.

Form: Rosette arrangement

Height: 8 to 10 cm.
Growth: Moderate, petioles at first upright, becoming horizontal with age.
Size: Medium to 21 cm. in diameter.
Mutation prone: None observed for flowers or foliage.
Foliage:
- *Shape.*—Ovate, slight cordate base, rounded tip, slight crenate margin.
- *Length.*—7 to 8 cm. on mature leaves.
- *Width.*—6 to 7 cm. on mature leaves.
- *Color.*—Upperside: Dark green. Underside: Pale green.
- *Texture.*—Upperside: Pubescent. Underside: Puberulent.
- *Ribs and veins.*—Pronounced, pinnate, red pigmented.
- *Petiole.*—Flattened above, pubescent, red pigmented.

THE FLOWER

Blooming habit: Continuous and abundant under optimal growing conditions.
Number: 6 to 10 per peduncle.
Size of Flower: Each flower is approximately 3 to 4 cm. in diameter.
Color: Red-Purple, RHS 74A.
Type: Single.
Petals: Five per individual flower with margins ruffled.
Texture: Smooth, slightly flexible.
Appearance: Upperside glabrous, lowerside slightly puberulent.
Peduncles: 6 to 7 cm. in height, pubescent, red pigmented.
Inflorescence: Cyme, upright, above the foliage.
Calyx: Quinquepartite, red pigmented, puberulent.
Persistence: Flowers do not drop.
Fragrance: None.

REPRODUCTIVE ORGANS

Stamen: Usually two per flower.
Anthers: Bright yellow, basifixed, two per filament.
Filaments: c. 0.3 cm. in length.
Pollen: Light yellow.
Pistils: One.
- *Stigma.*—Visible and accessible, becoming swollen when receptive and exuding a droplet of clear liquid.
- *Style.*—c. 0.7 cm. in length.
- *Ovary.*—Superior.

I claim:

1. A new and distinct cultivar of African violet named 'Katy', as described and illustrated, and particularly characterized by its profuse flowering, upright flower stems, compact bouquet, vigorous growth habit, flowers 11 to 12 weeks after potting and its long lasting and non-dropping flowers which gives the plant a substantially continuous beauty.

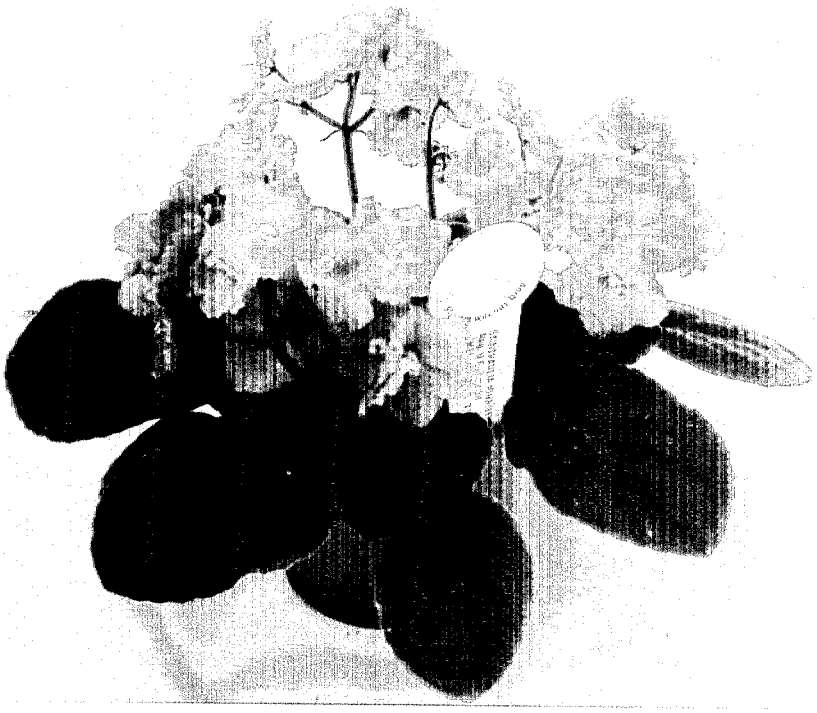

* * * * *